United States Patent [19]

Kessler et al.

[11] Patent Number: 4,518,992
[45] Date of Patent: May 21, 1985

[54] ACOUSTIC IMAGING SYSTEM AND METHOD

[75] Inventors: Lawrence W. Kessler, Glenview; Donald E. Yuhas, Wood Dale, both of Ill.

[73] Assignee: Sonoscan, Inc., Bensenville, Ill.

[21] Appl. No.: 442,264

[22] Filed: Nov. 17, 1982

[51] Int. Cl.³ .............................................. H04N 5/30
[52] U.S. Cl. .................................. 358/112; 358/174; 73/606; 367/7
[58] Field of Search ............... 358/110, 112, 174, 139; 455/604, 614; 73/606, 603; 367/7, 191, 900

[56] References Cited

U.S. PATENT DOCUMENTS

| | | | |
|---|---|---|---|
| 3,585,848 | 6/1971 | Korpel | 73/603 |
| 3,590,681 | 7/1971 | Cross | 455/605 |
| 3,611,277 | 10/1971 | Yoder | 455/605 |
| 3,622,791 | 11/1971 | Bernard | 455/614 |
| 3,790,281 | 2/1974 | Kessler et al. | 367/191 |
| 3,903,497 | 9/1975 | Stimler et al. | 455/614 |
| 3,937,066 | 2/1976 | Green et al. | 367/7 |
| 4,012,951 | 3/1977 | Kessler | 73/606 |

*Primary Examiner*—John C. Martin
*Assistant Examiner*—Edward L. Coles

*Attorney, Agent, or Firm*—Kinzer, Plyer, Dorn & McEachran

[57] ABSTRACT

An acoustic microscope or like acoustic imaging system includes an insonifier for insonifying an object with high frequency (over ten megahertz) acoustic waves, a scanner for scanning a high-energy light beam across a reflective interface surface coupled to the object, a photodetector to detect the reflected beam, and a signal processor to convert the photodetector output to an image signal used to produce a visual image representative of acoustic properties of the object; the level of the image signal is detected and is used to adjust the gain of the insonifier to a reference level, the insonification gain adjustment affording a quantitative measure of acoustic properties of the object, usable for comparison purposes, that minimizes or eliminates the effects of system non-linearities and compensates for inadequate dynamic range of system components. The quantitative measurement can be limited to a portion of the object, for comparison with another part of the same object or with a part of another object, and the portions of the image corresponding to the quantitative measurements can be visually identified. An optical AGC circuit is provided to compensate for non-uniformity in operation of the optical scanner and photodetector.

51 Claims, 5 Drawing Figures

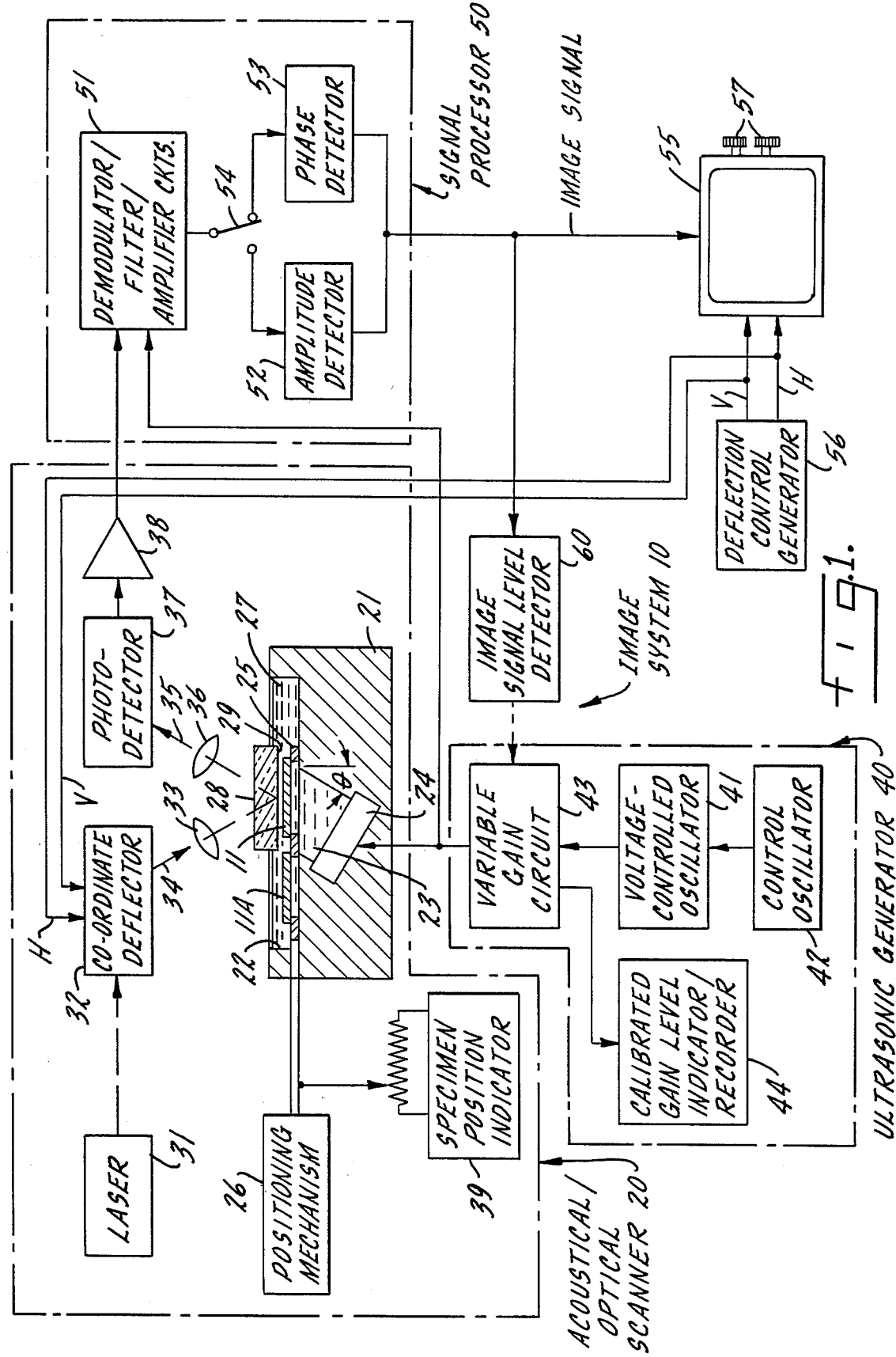

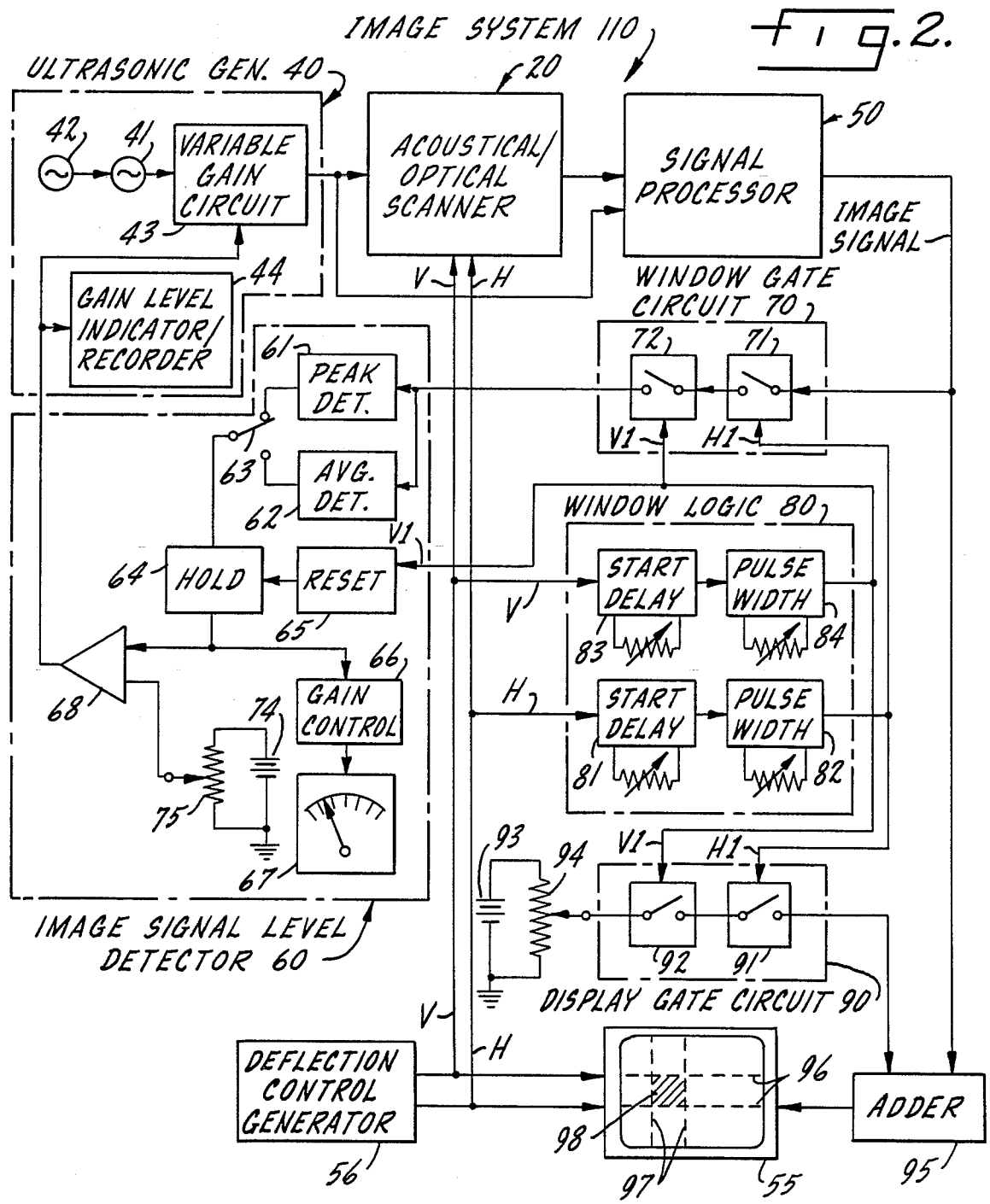

ACOUSTIC IMAGING SYSTEM AND METHOD

BACKGROUND OF THE INVENTION

Acoustic microscopes and other similar acoustic inspection systems are utilized to determine physical characteristics of objects that cannot be ascertained by more conventional optical examination techniques. Early examples of scanning laser acoustic microscopes are presented in U.S. Pat. Nos. 3,585,848 and 3,790,281; a more effective scanning laser acoustic microscope is disclosed in U.S. Pat. No. 4,012,951. These acoustic microscopes make it possible to visualize localized variations in elastic properties, particularly the density and elastic modulus (or its reciprocal, compressibility), for a wide variety of different objects.

Defects and other variations in a sample object, such as flaws in laminations or variations in density or porosity, act as attenuators or scatterers for the acoustic beam in an acoustic microscope. That is, localized structural features in an object subjected to examination in an acoustic microscope differentially attenuate, absorb, or reflect acoustic energy to produce patterns of light and dark features (grey scale) within an acoustic image produced as the output of the microscope. Quantification of acoustic properties within the object under examination, particularly if effected on a localized regional basis, can be of substantial importance in providing a basis for identifying defects in the object. The amplitude level of the image signal used to develop the acoustic image is generally responsive to the localized acoustic signal level, so that measurement of image signal level may be taken as a first step toward quantification of the image information.

However, there are a number of substantial problems associated with measurement of the amplitude level of the acoustic image signal which make that signal level unreliable as a direct source of quantified data pertaining to the acoustical properties of an object under examination. Thus, in the present state of the art the dynamic ranges of the amplifiers, detectors, and other circuits utilized to develop the acoustic image signal are often insufficient to allow for accurate reproduction, on a quantified basis, of the localized attenuation characteristics of an object subject to inspection in an acoustic microscope. This is also true of the available cathode ray tube image display devices, which have a rather limited dynamic range.

Another problem is that the detection, demodulation, and other signal processing circuits incorporated in an acoustic microscope are not usually linear over the entire dynamic range of operation for the microscope. This non-linearity difficulty applies also to the cathode ray tube displays usually used to produce the acoustic image output. These non-linearities effectively preclude a valid quantitative comparison between high and low image signal levels. To some extent, this may be rectified by calibration of the circuits and the display, based on samples having known acoustic properties. However, even such calibration can prove ineffective due to the fact that the gain characteristics of amplifiers and the impedance values of other electronic components may drift over extended periods of time. Such drift also occurs with temperature changes, especially during the warm-up cycle for the acoustic imaging system. Thus, an ordinary calibration technique applied to the demodulation, detection, signal processing, and display equipment may require repetition for each measurement, a time-consuming and inefficient procedure.

Another inhibition with respect to quantitative comparison of data from acoustic imaging systems results from the fact that the image signal contains data for a complete field of view defined by the scanned area of the object under test. This makes it difficult to compare one area of a given sample object to another area of the same object, or even to obtain quantitative information specific to a limited portion of an object being subjected to acoustic inspection. Further, there is no effective technique for useful quantitative comparison of limited portions of two different objects.

In an acoustic imaging system that employs optical (light beam) scanning, any non-uniformity of the scanning illumination intensity can cause errors in interpretation and quantification of the acoustic image. Such non-uniformity may result from non-uniform deflection in the scanning system, from stage misalignment relative to the photodetector, from non-uniform photodetector response characteristics, from variations in a reflective surface incorporated in the scanner, or from a number of other causes. Elimination of such scanner-induced errors may be essential to effective operation of a scanning acoustic microscope, particularly when employed for quantitative as well as qualitative measurements.

Throughout this application the terms "acoustic imaging system" and "acoustic microscope" are used interchangeably; an acoustic microscope constitutes any acoustic imaging system affording any degree of magnification. Further, both terms are intended to encompass combined acoustic-optical imaging systems (microscopes) that provide both acoustic images and optical images of an object under examination, as in the system disclosed in U.S. Pat. No. 4,012,951.

SUMMARY OF THE INVENTION

It is an object of the present invention, therefore, to provide a new and improved acoustic imaging method and apparatus that effectively and inherently minimizes or overcomes the difficulties referred to above.

A particular object of the present invention is to provide a new and improved acoustic imaging system and method that effectively compensate for lack of adequate dynamic range in the components of an acoustic microscope system and thus permit useful quantification of the results of operation of the system.

Another particular object of the invention is to provide a new and improved acoustic imaging system and method that effectively compensate for non-linearities in the acoustic, optical, and electronic components of an acoustic microscope system to allow for useful quantification of the results of operation of the system.

Another object of the invention is to provide a new and improved method and apparatus for an acoustic microscope system that allow for effective selection of limited portions of an overall scanning field for quantitative measurement and comparison purposes, permitting variation of the size and position of the selected portion to cover any selected part of the scanning field.

Another object of the invention is to provide a method and apparatus for quantified measurement and comparison of limited portions of a scanning field, in an acoustic microscope system, that afford the system operator effective visual identification of parts of the scanning field that are being subjected to quantitative measurement and comparison.

Yet another object of the present invention is to provide a new and improved method and apparatus for use in an acoustic imaging system which makes it possible to obtain effectively quantified and comparable measurements of limited portions of a series of different objects, suitable for comparison.

Accordingly, the present invention relates to an improved acoustic imaging system for generating a visual image representative of the acoustic properties of an object, of the kind including insonification means for insonifying the object with acoustic waves having a frequency above ten megahertz to develop a pattern of perturbations on an at least partially light-reflective interface surface, coupled to the object, which pattern is representative of acoustic properties of the object, scanning means for scanning a high-energy small-diameter light beam across the interface surface, photodetection means for detecting a portion of the light beam reflected from the interface surface to develop an initial electrical signal, signal processing means, coupled to the photodetection means, for processing the initial electrical signal to develop an acoustic image signal, and display means, coupled to the signal processor means, for utilizing the image signal to develop a visual image representative of acoustic properties of the object.

In one aspect of the invention, the system improvement comprises image signal level determination means, coupled to the signal processor means, for detecting the amplitude level of the image signal, and variable gain means, incorporated in the insonification means, for adjusting the intensity of the acoustic waves insonifying the object to afford an image signal level corresponding to a given reference level, the adjustment of the variable gain means affording a quantitative measure of variation of acoustic properties of the object, relative to the reference, that minimizes the effects of inadequate dynamic range and non-linearities in the imaging system.

In another aspect of the invention, the system improvement comprises low pass filter means, coupled to the photodetection means, for developing an optical content signal from the initial electrical signal, comparator means for comparing the optical content signal with a given reference signal level to develop a gain control signal, and gain control means, interposed between the photodetection means and the signal processor means, responsive to the gain control signal, for varying the amplitude of the initial signal supplied to the signal processor means to minimize the effects of non-uniformity in operation of the scanning means and photodetection means.

Further, the invention relates to a method of acoustic imaging comprising the basic steps of:

A. scanning a high-energy small diameter light beam across an at least partially light-reflective interface surface coupled to an object to be examined;

B. insonifying the object with acoustic waves having a frequency above ten megahertz to develop a pattern of perturbations at the interface surface, which pattern is representative of acoustic properties of the object;

C. detecting a portion of the light beam reflected from the interface surface to develop an initial electrical signal;

D. processing the initial electrical signal to develop an acoustic image signal;

E. and utilizing the image signal to develop a visual image representative of acoustic properties of the object.

In one aspect of the invention, the method improvement comprises:

F. detecting the amplitude level of the image signal;

G. adjusting the intensity of the acoustic waves insonifying the object to afford an image signal level corresponding to a given reference level; and H. recording the adjustment of acoustic wave intensity as a quantitative measure of variation of acoustic properties of the object, relative to the reference, that minimizes the effects of inadequate dynamic range and nonlinearities in the imaging system.

In another aspect of the invention, the method improvement comprises:

J. developing an optical content signal from the initial electrical signal of step C, using low pass filter means; and K. using the optical content signal to control the amplitude of the acoustic image signal to compensate for non-uniformities occurring in the scanning and detecting operations of steps A and C.

BRIEF DESCRIPTION OF THE DRAWINGS

FIG. 1 is a block diagram of an acoustic imaging system constructed in accordance with a basic embodiment of the present invention;

FIG. 2 is a block diagram illustrating a more sophisticated embodiment of the invention, a modification of the system shown in FIG. 1, with additional operational features;

FIG. 3 is an explanatory diagram of particular gating signals employed in the imaging system of FIG. 2;

DESCRIPTION OF THE PREFERRED EMBODIMENTS

Figure 4:
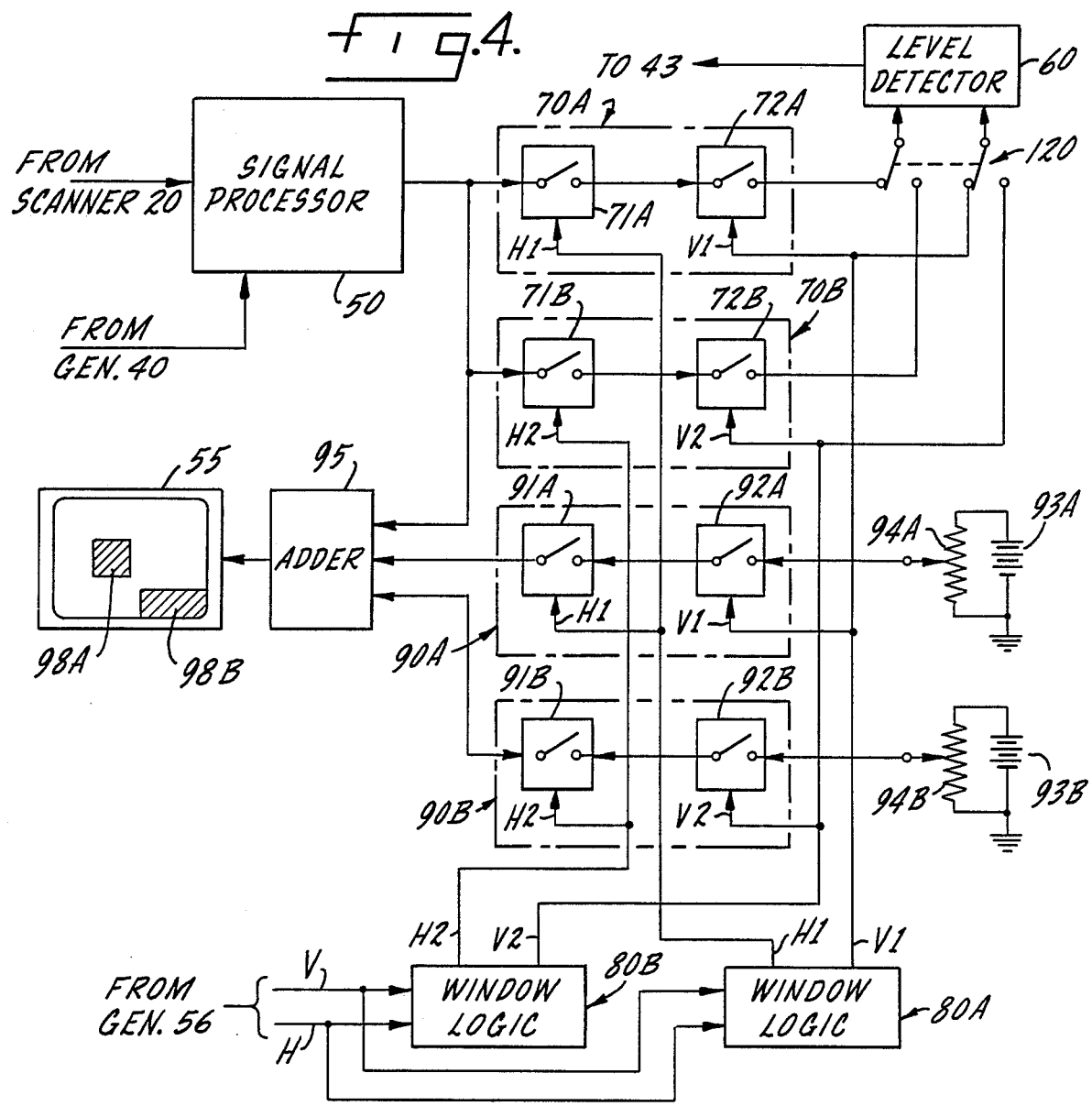
FIG. 4 is a block diagram illustrating a further modification of the system of FIG. 2, utilized for plural comparisons within a single scanning field.

The acoustic imaging systems of the present invention utilize a distortion that occurs at an elastically deformable interface surface, having finite acoustic impedance, when the interface is subject to an incident acoustic wave. Thus, when an elastically deformable interface surface intercepts an incident plane wave $I_s$ having a velocity V, at an angle of incidence $\theta$, the acoustic wave produces a dynamic pattern of perturbations on that surface, sometimes called a ripple pattern, with fluctuations occurring at the acoustic frequency. The phase of the pattern or displacement wave propagates at a velocity V', with $$V' = V/\sin \theta.$$

In one form of acoustic microscope, as described in "An Acoustic Microscope Operating at 100 Mhz", Nature, Vol. 232, page 110 (1971), the interface is formed by a plastic resin coverslip mounted on a sound cell or stage filled with water or other sonic propagation fluid medium. The acoustic impedance of a resin coverslip can be reasonably matched with water; moreover, because the resin is quite lossy, acoustically, acoustic energy transmitted to the coverslip can be effectively propagated into space, thereby avoiding resonance effects. The pattern of perturbations on the coverslip is made optically reflective by a metallic coating on the interface surface. The interface is scanned with a focused laser beam, producing a reflected beam angularly modulated by the changes in slope of the pattern. The reflected beam is selectively detected to develop an electrical signal coherent with the local sound pressure at the interface.

An object to be subjected to acoustical examination, placed just under the coverslip, modifies the perturbation pattern in accordance with acoustic properties of the object. For inspection of an object of substantial thickness, or in other instances in which the plane of interest in the object cannot be located immediately adjacent the coverslip, the phase of the signal developed from the reflected beam can be analyzed to produce an acoustic hologram of the object; the hologram can subsequently be reconstructed optically in accordance with known techniques. For specific coverslip materials, resolution characteristics, and preferred angles of incidence, reference may be made to U.S. Pat. No. 3,790,281. A similar arrangement can be used with no coverslip, provided the object under test has a smooth, polished, reflective surface that can serve as the scanning interface surface.

FIG. 1 illustrates an acoustic imaging system 10, constituting an acoustic microscope, constructed in accordance with a preferred embodiment of the present invention. Imaging system 10 is utilized for acoustic examination or inspection of an object 11, sometimes referred to as a specimen or sample. Imaging system 10 comprises an acoustical/optical scanner 20 including a base or stage 21 formed with an upwardly facing chamber 22 having an oblique downwardly extending chamber extension 23 aligned at an angle $\theta$ with respect to the chamber. An electro-acoustical transducer 24 is mounted in stage 21 at the bottom of chamber extension 23.

A specimen support member 25 may be utilized to support specimen 11 within the chamber in stage 21, in alignment with chamber extension 23 and transducer 24. Support member 25 may be connected to a positioning mechanism 26 utilized to adjust the alignment of specimen 11 relative to transducer 24. An indicator 39 may be provided to show the position of object 11 in stage 21.

The acoustical/optical scanner 20 further comprises boundary means defining an elastically deformable and at least partially light reflective interface surface that is coupled to object 11 by a fluid sonic propagation medium 27 that fills chamber 22 and chamber extension 23. The fluid medium 27, in most instances, is water. The boundary means may comprise a transparent coverslip 28 formed of a resin such as a polymethylmethacrylate or polycarbonate; coverslip 28 is mounted on a suitable support mechanism (not shown) and is positioned immediately above the open end of chamber extension 23, thus being located immediately over the specimen or object 11. The bottom surface 29 of coverslip 28 is preferably immersed in the fluid propagation medium 27. Surface 29 is coated with a thin, vacuum-deposited metal coating or is otherwise treated to be at least partially light reflective. Thus, surface 29 of coverslip 28 affords an elastically deformable and at least partially light reflective interface surface coupled to the object 11 by the fluid propagation medium 27.

Scanner 20 can also be employed without coverslip 28 if the upper surface of object 11 is a smooth, polished, light reflecting surface. In that arrangement, the level of fluid 27 in chamber 22 should be low enough so that the top surface of object 11 is exposed and can serve as a substitute for interface surface 29.

Acoustical/optical scanner 20 incorporates scanning means for scanning a high-energy light beam of very small diameter across the interface surface 29, or across the top surface of object 11 when that surface is used as the interface. This scanning means comprises a laser 31 which generates a small, intense, coherent light beam. The beam from laser 31 passes through a coordinate deflector 32 and a lens 33, traversing a path 34 to impinge as a tightly focussed light spot on interface surface 29. The coordinate deflector 32 may comprise a pair of light deflector cells of the kind described in "A Television Display Using Acoustical Deflection and Modulation of Coherent Light", *Applied Optics*, Volume 5, page 1667 (1966). Horizontal and vertical deflection of light beam 34, in deflector 32, are controlled by two electrical input signals H and V, the source of these signals being identified below.

The incident light beam 34 is reflected from interface surface 29 along a path 35, passing through a lens 36 to impinge upon a photodetector 37. Photodetector 37 may comprise a knife edge or mask deflector, positioned to block one-half of the reflected light beam 35, thus constituting a photodetection means of the kind described in the aforementioned U.S. patents. On the other hand, other effective photodetection means are known in the art; for example, see U.S. Pat. Nos. 4,019,818 and 4,180,324.

Imaging system 10 further comprises an ultrasonic excitation signal generator 40. The ultrasonic generator 40, in the preferred arrangement shown in FIG. 1, comprises a voltage controlled oscillator 41 having an operating frequency in excess of ten megahertz. Preferably, the frequency range for oscillator 41 is thirty megahertz or higher; frequencies of up to five hundred megahertz are used. Ultrasonic generator 40 may include a control oscillator 42 for continuous modulation of the operating frequency of oscillator 41 to enable imaging system 10 to provide speckle elimination and other desirable attributes described in U.S. Pat. No. 4,012,951. The output of oscillator 41 is coupled to transducer 24 to drive the transducer.

Photodetector 37 in scanner 20 develops an initial electrical signal representative of acoustical properties of the specimen 11 under test. That initial electrical signal is supplied, through a preamplifier 38, to a signal processor circuit 50 incorporated in image system 10. Signal processor 50 comprises demodulator, filter and amplifier circuits shown only generally as circuit unit 51. Circuit unit 51 may include all of the heterodyning and other operating circuits illustrated as "filter means" 47 in the aforementioned U.S. Pat. No. 4,012,951, and may require a heterodyning input from ultrasonic generator 40. The output of circuit unit 51 is supplied, through a selector switch 54, to either an amplitude detector 52 or a phase detector 53; the phase detector requires an additional reference input from circuit unit 51. The detector output is an acoustic image signal that is supplied to a display means 55. The display means may constitute a conventional television monitor having the usual brightness, contrast, and other controls 57.

Deflection control signals H and V, to control the horizontal and vertical scanning functions of display 55, are provided by a deflection control signal generator 56. Assuming that display 55 is a conventional television monitor, the frequencies and relationship of deflection control signals H and V may be the same as for ordinary commercial television. These deflection control signals H and V are also supplied to the coordinate deflector 32 in the acoustical/optical scanner 20, so that the scanner operates in synchronism with the image raster of display 55.

As thus far described, the acoustic microscope or imaging system 10 is essentially conventional. Accordingly, only a brief description of its operation is required. Transducer 24, energized from ultrasonic generator 40, effectively insonifies an object 11 with acoustic waves having a frequency above ten MHz, preferably thirty MHz or higher, to develop a pattern of perturbations on the interface surface 29, that pattern being representative of acoustic properties of object 11. The ripple pattern on the interface surface is scanned with the high-energy, small diameter light beam generated by laser 31, under the control of coordinate deflector 30, with the horizontal and vertical scanning rates controlled by deflection signals H and V from control generator 56. A portion of the light beam reflected from interface surface 29 is detected by the photodetector 37, developing an initial electrical signal that is supplied to the demodulator/filter/amplifier circuits 51 of signal processor 50. The output signal from circuit unit 51 is detected, either in amplitude detector 52 or phase detector 53, thereby developing an acoustic image signal that is supplied to display 55. Display 55, which has its image raster controlled by the deflection signals H and V that control beam deflector 32, utilizes the acoustic image signal from signal processor 50 to produce a visual image that is representative of acoustic properties of object 11.

In image system 10, FIG. 1, a variable gain circuit 43 is incorporated in ultrasonic generator 40, interposed between the voltage-controlled oscillator 41 and the transducer 24 in scanner 20. The variable gain circuit 43 may be an adjustable gain amplifier or a variable attenuator; either type of variable gain circuit can be effectively employed. In the simplest arrangement, circuit 43 may be manually adjustable to vary the amplitude of the excitation signal supplied to transducer 24 and thereby adjust the intensity of the acoustic waves that insonify object 11. In more sophisticated embodiments, as described hereinafter, the variable gain circuit 43 may be a signal-responsive amplifier or attenuator to permit closed loop control of the insonification intensity.

A gain level indicator 44 is operatively connected to the variable gain circuit 43 in ultrasonic generator 40. For a manually controlled variable gain circuit 43, indicator 44 may comprise a calibrated scale associated with the manual adjustment for circuit 43. In those instances in which circuit 43 is a signal-responsive amplifier or attenuator, the gain level indicator 44 may comprise a meter or other like device responsive to a signal from circuit 43 indicative of the gain adjustment. Device 44 may also include a recorder.

The imaging system 10 of FIG. 1 further comprises an image signal level detector 60 having an input connection from the output circuit of signal processor 50 that supplies an image signal to display 55. Detector 60 may comprise a peak detector or a signal averaging detector; the desired function is to provide an indication of the overall amplitude level of the image signal being supplied to display 55. Thus, in those instances in which variable gain circuit 43 is manually actuated, the image signal level detector may include a meter to enable the operator of imaging system 10 to determine the image signal level visually and make an adjustment of variable gain circuit 43 to restore the image signal level to a given reference. In more sophisticated embodiments of the invention, as discussed hereinafter, the image signal level detector may be a part of a closed loop control for a signal-responsive variable gain circuit 43.

Prior to operation of image system 10 in the testing or study of an object 11 having unknown acoustic properties, system calibration is highly desirable. As previously discussed, the amplifiers, the detectors, the picture tube, and other components of image system 10, particularly in signal processor 50 and display 55, may be inadequate in dynamic range for accurate reproduction of the acoustic attenuation characteristics of an unknown sample. Furthermore, these same system components are often non-linear, at least over parts of their operating ranges, and amplifier gains and electronic component values may drift with time or with temperature changes, particularly during a warm-up cycle for system 10.

To calibrate image system 10, a series of measurements may be taken using acoustic objects of known properties. This series can start with no object 11 of any kind in acoustic scanner 20, so that the only attenuation of the acoustic waves impinging upon interface surface 29 is that introduced by the presence of the fluid coupling medium 27 (water). With a series of objects having known acoustic attenuation properties, it is possible to calibrate the system to enable indicator 44 to afford quantitatively comparable indications of the attenuation properties of unknown samples in the course of subsequent tests. Thus, in any test of an unknown object, the variable gain circuit 43 in the insonification means comprising ultrasonic generator 40 and transducer 24 is adjusted until the image signal level detector 60 indicates that a known reference level for the image signal has been achieved. The extent of this adjustment is indicated by the calibrated gain level indicator 44 and affords quantitative data relative to the attenuation properties of the sample under test that are substantially more accurate than a direct reading from the image signal level detector 60. Specific operating techniques applicable to system 10, for quantitative measurements, are described below.

Image system 10, FIG. 1, provides quantitative comparison data only for the entire scanning field of the acoustical/optical scanner 20, as reproduced by display 55. In many instances, this information is inadequate due to appreciable variations in the acoustic properties for different areas of the sample 11 under test. This is particularly true with regard to an object 11 that has small localized aberrations or defects; for such a sample, it is often essential, for effective inspection, to be able to obtain quantitative acoustic property information with respect to a limited portion of the object in order to establish whether a localized variation represents an actual defect or constitutes a harmless anomaly.

FIG. 2 illustrates an acoustic imaging system 110 that is essentially similar to the previously described system 10 but which incorporates a substantially more effective arrangement for obtaining quantitative acoustic data with respect to a sample under test, data that can be restricted to any limited portion of the sample.

Imaging system 110 comprises an acoustical/optical scanner 20 having an insonification excitation input signal from an ultrasonic generator 40 and developing an output signal that is supplied to a signal processor 50 that generates an acoustic image signal which is used in a display 55 to develop a visual image representative of acoustic properties of an object. Scanning deflection and display deflection are both controlled by appropriate horizontal and vertical deflection signals H and V from a deflection control generator 56. Scanner 20, signal processor 50, display 55, and deflection control generator 56, may all be as described above in connection with FIG. 1. In this instance, circuit 43 in ultrasonic generator 40 is shown as a signal-responsive variable gain amplifier or attenuator.

In image system 110, FIG. 2, the image signal level detector 60 includes a peak detector 61 and an averaging detector 62. The outputs of the two detectors 61 and 62 are supplied, through a selector switch 63, to a hold circuit or integrator 64 for integrating the detector output over a given time interval, that time interval being determined by an input to hold circuit 64 from a reset circuit 65. The output of hold circuit 64 is supplied, through a gain control circuit 66, to an indicator 67, shown as a conventional meter. The output of hold circuit 64 is also connected, through a comparator amplifier 68, to the gain control input of the variable gain circuit 43 in ultrasonic generator 40. Amplifier 68 also has a reference input from an adjustable D.C. source shown as a battery 74 and potentiometer 75. The output from comparator amplifier 68 may also be connected as an input to the indicator/recorder 44.

The image signal inputs to the two peak detectors 61 and 62 in image signal level detector circuit 60 are derived through a window gate circuit 70. Window gate 70 comprises two series connected signal-actuated switches, a horizontal switch 71 and a vertical switch 72. Preferably, these two switches are signal-actuated solid state gates; transistors can be utilized. The two gates are shown with the horizontal gate 71 connected ahead of the vertical gate 72, but this relationship could be reversed without affecting operation.

The control of the horizontal and vertical switches 71 and 72 in window gate circuit 70 is provided by a window logic circuit 80. Window logic 80 comprises an adjustable start delay circuit 81 having an input constituting or derived from the horizontal deflection control signal H from deflection control generator 56. The start delay circuit 81 is connected in series with an adjustable pulse width delay circuit 82, the output from circuit 82 constituting an actuating signal that is applied to the horizontal switch 71 in window gate circuit 70 as a switch-closing signal H1.

The window logic 80 further comprises another adjustable start delay circuit 83, the input to circuit 83 being derived from the vertical deflection signal V of deflection control generator 56. The start delay circuit 83 is connected in series with an adjustable pulse width delay circuit 84. The output from circuit 84 is a switching signal V1 that is supplied to horizontal switch 72 in window gate circuit 70 to actuate that switch. The vertical actuation signal V1 is also connected as an input signal to reset circuit 65 in the image signal level detector 60.

Image system 110 (FIG. 2) further comprises a display gate circuit 90 that is a substantial duplicate of window gate circuit 70. Display gate circuit 90 includes a horizontal gate 91 connected in series with a vertical gate 92. The input to circuit 90 is taken from a variable DC supply shown schematically as a battery 93 and a potentiometer 94. The output from display gate circuit 90 is connected to an adder circuit 95 interposed in the image signal circuit between signal processor 50 and display 55.

Perhaps the best starting point for discussion of operation of image system 110 of FIG. 2 is a functional description of window logic circuit 80, with reference to FIG. 3. The upper portion of FIG. 3 shows two pulses H representative of the horizontal deflection signal from deflection control generator 56; the space between the pulses H corresponds to the time required for a horizontal line trace in display 55 and for a horizontal line scan interval in acoustic scanner 20. It will be recognized that the actual signal H output from deflection control generator 56 may be a ramp signal; the deflection signal has been illustrated as a sequence of pulses in FIG. 3 simply for convenience.

A horizontal deflection pulse signal H input to the horizontal start delay circuit 81 (FIG. 2) produces no output from the start delay circuit until after a predetermined delay interval. That start delay interval can be adjusted to any point within the line trace. When the delay interval of circuit 81 has expired, an output signal H1 (FIG. 3) is initiated and is supplied to the window gate circuit 70 and the display gate circuit 90 (FIG. 2). After a further pulse width delay, determined by the adjustment of pulse width circuit 82, the horizontal gate signal H1 is terminated. Thus, during each horizontal trace of display 55, the horizontal gates 71 and 91 in circuits 70 and 90 (FIG. 2) are closed. For the example shown in FIG. 3, this means that the gates are closed during the portion of each horizontal trace indicated by the dash lines 97 on display 55 in FIG. 2.

The vertical start delay circuit 83 and pulse width circuit 84 in window logic 80 function in the same manner. Referring to FIG. 3, the duration of a vertical scan interval is indicated by two pulses V, representative of the vertical sweep signal output from deflection control generator 56 (FIG. 2). Again, the actual signal V may be a ramp signal. It will be understood that the time scales for signals H and V, in FIG. 3, are not comparable; in actual practice, the time of one vertical interval V—V exceeds a horizontal trace interval H—H by a factor of several hundred.

Each vertical deflection signal V (FIG. 3) initiates a start delay interval, determined by the setting of circuit 83; after expiration of the start delay, a vertical gate control signal V1 is initiated and is supplied to gates 72 and 92 (FIG. 2) to close those gates. The period during which the vertical gates 72 and 92 remain closed is determined by the setting of the vertical pulse width delay circuit 84, which cuts off signal V1 when its time delay expires. As in the case of the horizontal gate control signal, the vertical gate control signal V1 can be varied, by adjustment of circuits 81 and 82, to occupy any desired portion of the vertical sweep interval for display 55. For the situation illustrated in FIG. 3, the duration of vertical gate control signal V1 corresponds to that portion of the image on display 55 identified by dash lines 96. It is thus seen that the horizontal and vertical gate control signals H1 and V1 conjointly define a limited portion 98 of the image produced by display 55 and can be varied to change the size of image portion 98 and its position within the overall image. Because scanner 20 and display 55 operate in synchronism, the limited image portion 98 corresponds to a preselected part of the object 11 under examination.

In operation of imaging system 110, FIG. 2, therefore, whenever the limited portion 98 of the image on display 55 is being reproduced, the two switches 71 and 72 of window gate circuit 70 are closed and the image signal from signal processor 50 is supplied to the inputs of the two detectors 61 and 62 in image signal level detector 60. Only one of the detectors 61,62 is used at any given time, selection being effected by switch 63. The selected output is supplied to hold circuit 64, which is reset at the beginning of each vertical gate control signal V1 by operation of reset circuit 65. The output of hold circuit 64 is supplied to meter 67 through gain control circuit 66 to afford a direct quantitative indication of the level of the image signal. This could be used by a system operator to adjust the variable gain circuit 43 of ultrasonic generator 40 to obtain a reference level at meter 67, if a manual variable gain circuit were utilized. With the complete illustrated arrangement, on the other hand, the output from hold circuit 64 is supplied to variable gain circuit 43 as a closed loop feedback to adjust the insonification intensity in a manner that maintains an essentially constant image signal output level from signal processor 50. With this closed loop arrangement, quantitative information is derived by recording variations of the output signal from hold circuit 64, relative to the reference level determined by source 74,75. In this manner, quantitative measurement of variations in the level of the image signal, indicative of acoustic properties of the sample under test, are obtained in image system 110, based on changes of the gain in circuit 43.

In the inspection of a given object or sample, the system operator may want to obtain quantitative information about various limited portions of that sample. This can be readily accomplished because the limited portion 98 for which quantitative data is obtained can be readily changed to suit the requirements of the situation simply by adjustment of the four delay circuits 81–84 in window logic 80. That is, the location and size of the specific limited portion 98 of the image on display 55, which corresponds to a specific limited part of the object under test, can be shifted as desired by the system operator. In this regard, it may be noted that circuits 81–84 in window logic 80 need not be analog delay circuits; for precise positioning of the limited area 98 selected for quantitative measurement, digital countdown circuits can be employed in the construction of window logic 80.

It is usually helpful to provide the system operator with a direct indication, on display 55 that will identify the specific limited area 98 being examined for the development of quantitative acoustic data. This is accomplished by display gate circuit 90, in which the horizontal and vertical switches 91 and 92 are closed for the same time intervals as the window gates 71 and 72. In the illustrated arrangement, this is accomplished simply by adding a small DC increment to the image signal supplied to display 55, by means of adder 95. This effectively "highlights" the limited area 98 being subjected to quantitative measurement. It will be recognized that other circuit arrangements of more complex nature, utilizing the output from display gate circuit 90, can be employed to form a visual "frame" around the quantitative test portion 98 of the display, instead of or in addition to highlighting that portion of the display, if desired.

For a more complete understanding of the capabilities of image system 110, consideration may be given to specific operating procedures. For initial discussion purposes, it will be assumed that the feedback circuit comprising amplifier 68 is not present and that device 44 is actuated from circuit 43.

In order to obtain quantitative information for comparison of two different objects, the operator of system 110 may start by positioning the first object 11 in the stage 21 of scanner 20 (see FIG. 1). The operating parameters of the basic system components comprising scanner 20, ultrasonic generator 40, signal processor 50, and display 55 can then be adjusted, as in a conventional scanning laser acoustic microscope, to obtain an acoustic image of the first object, at acceptable levels of brightness and contrast, on display 55. This is effected with the variable gain circuit 43 set to a reference level. Window logic 80 is adjusted to define a desired area 98, as to both size and position in the image on display 55.

Selector switch 63 is actuated to select either peak detector 61 or average detector 62. Gain control 66 is adjusted to set the output indicator 67 to a reference level; for example, gain control 66 may be adjusted so that the pointer is at mid-scale for indicator 67 where a meter is used as the indicator.

The first object 11 is then withdrawn from the the stage 21 of acoustical/optical scanner 20, leaving only the coupling fluid 27 (usually water) between transducer 24 and the interface surface 29 of coverslip 28 (see FIG. 1). This results in a change of the reading of indicator 67 (FIG. 2) due to the different image signal level produced by the change in the acoustic coupling between the transducer and the coverslip. Usually, the indicator 67 will show a higher image level.

At this point in the procedure, variable gain circuit 43 is adjusted to an insonification intensity that restores indicator 67 to the reference level previously established with the first object. The change in gain of circuit 43 required to accomplish this result represents the quantitative measurement of the desired limited portion 98 for the first sample, and may be recorded by device 44.

A second sample object is now positioned in scanner 20 in the insonification path between transducer 24 and coverslip 28, and the variable gain circuit 43 is readjusted to its original setting. The desired limited area selected for comparison purposes, relative to this second object, may be the same, or it may be different; if different, window logic 80 is adjusted to select the desired limited part of the second sample for comparison purposes. The procedure followed for the first object is repeated, resulting in the recording of an attenuation level representative of acoustic properties of the second object. The two values recorded for the two objects are directly comparable and afford a quantitative comparison of the acoustic properties of those two objects.

In essentially the same manner, a quantitative comparison may be effected for two or more portions of a single test object or sample 11. The test object 11 is mounted in stage 21 of acoustic scanner 20 as shown in FIG. 1 and window logic 80 is adjusted to select a first area of interest 98 for quantitative inspection. The variable gain circuit 43 is adjusted to a reference position and the setting is recorded. Window logic 80 is then adjusted to select a different limited portion 98; alternatively, a positioning mechanism such as device 26 may be employed to shift the position of the test object relative to transducer 24 and coverslip 28 in acoustic scanner 20 (FIG. 1). The gain of the variable gain circuit 43 is now adjusted upwardly or downwardly until indicator 67 reads the same as for the first inspected portion of the sample object. The new setting of variable gain circuit 43, as compared to the first setting, represents a quantitative difference in acoustic properties between the two limited parts of the sample. Of course, this procedure can be repeated for other individual limited portions of the sample; all of the quantitative data can be utilized for direct comparison.

In the two procedural examples just given, it has been assumed that there is no direct feedback loop connection from image signal level detector 60 to variable gain circuit 43. Operation in a closed feedback loop can now be considered.

Different portions of a given sample object 11 may exhibit substantial variations in ultrasonic attenuation; these differences give rise to the gray scale reproduced on display 55. Direct observation of the image signal output from signal processor 50 for a horizontal display line, on an oscilloscope, for example, reveals amplitude differences caused by regional ultrasonic attentuation differences within the test object. However, as stated before, these differences in amplitude of the image signal may not quantitatively represent the true differences in the test sample.

The feedback circuit arrangement illustrated in FIG. 2, utilizing amplifier 68 and the reference source 74,75, in conjunction with a linearized or calibrated variable gain circuit 43, is effective to resolve this difficulty. The output from comparator amplifier 68 is connected to the gain control of variable gain circuit 43. Thus, by setting an approximate reference level with potentiometer 75, the output of hold circuit 64 in image signal level detector 60 is maintained essentially constant despite changes in the position of the test object or adjustment of window logic 80 to change the portion of the test object under quantitative examination. In this situation, the relevant output signal is the output from amplifier 68, which affords a measure of the relative acoustic attenuation of the part of the sample object defined by window logic 80.

With this closed loop arrangement, there are two basic methods to obtain useful quantitative data. In the first, the window 98 defined by logic 80 is maintained fixed in size and position and the location of the test object on the stage of acoustic scanner 20 is varied, as by use of an appropriate positioning mechanism 26 (FIG. 1). The varying control voltage to the variable gain circuit 43, that is, the output of comparator amplifier 68, provides the quantitative data relating to different selected portions of the test object. This same arrangement can be utilized for comparison of two objects by positioning of a second test object 11A on the stage 21 of the scanner 20 (FIG. 1).

The second method leaves the test object 11 stationary but the specific area of the test object subjected to quantitative examination is changed by adjusting window logic 80 (FIG. 2). Again, the output of amplifier 68 provides the quantitative data to be used for comparison of acoustic properties of different portions of the sample under test. With respect to both techniques, it should be noted that the size of the inspection area 98 (FIG. 2) is larger than the minimum picture element of display 55, thereby optimizing the integration and compensating for unusual high contrast details in the acoustic image (such as speckle) which may not be of direct interest because they can mask general trend information.

FIG. 4 illustrates a system modification that permits display emphasis of two different limited areas of the overall scanning field. In this instance, the output of signal processor 50 is connected to a first window gate circuit 70A comprising a horizontal gate circuit 71A and a vertical gate 72A connected in series. The output from gate 72A is connected to the level detector circuit 60 through one pole of a double pole, double throw selector switch 120. The output of the signal processor is also connected to level detector 60 through a second window gate circuit 70B comprising, in series, a horizontal gate 71B and a vertical gate 72B, with the output of gate 72B connected to the alternate pole of selector switch 120 from the first window gate circuit 70A.

The dual selection circuit arrangement illustrated in FIG. 4 further comprises a first display gate circuit 90A including a horizontal gate 91A and a vertical gate 92A connected in series between a reference signal source 93A, 94A and the input adder circuit 95 for display 55. A second display gate circuit 90B, including a horizontal gate 91B and a vertical gate 92B, is connected from a reference supply 93B, 94B to adder circuit 95. As before, adder 95 receives a direct input of the image signal from signal processor 50 and the output of the adder constitutes the image signal input to display 55.

In the system modification shown in FIG. 4, there are two window logic circuits 80A and 80B, each of which is supplied with the horizontal and vertical synchronizing signals H and V from deflection control generator 56. Window logic circuit 80A produces two gate control signals, a horizontal gate control signal H1 and a vertical gate control signal V1. These are the actuating signals supplied to the horizontal and vertical gates in window gate circuit 70A and display gate circuit 90A. Window logic circuit 80A generates a horizontal gate control signal H2 and a vertical gate control signal V2 and these signals are applied as actuating signals to the horizontal and vertical gates in window gate circuit 70B and display gate circuit 90B. The horizontal and vertical gate control signals H1 and V1 define a first limited portion 98A of the image on display 55, whereas the gate signals H2 and V2 define a second limited portion 98B of the image on the display. Signals V1 and V2 are supplied to level detector circuit 60 through selector switch 120 for use as reset signals (See FIG. 2).

Thus, it is seen that the system modification shown in FIG. 4 highlights two distinct limited areas of the scanning field for specific observation by the system operator. For quantitative measurements, utilizing the image signal level detector 60, readings may be taken in sequence, utilizing the selector switch 120 to supply the image signal for area 98A to level detector 60, with signal V1 as a reset signal, or to supply the image signal pertaining to area 98B to the level detector along with the signal V2 as a reset signal. In all other respects, the operation of the system modification shown in FIG. 4 is the same as described above in connection with FIG. 2.

In an acoustic imaging system (microscope) adapted to quantitative analysis, non-uniformity of the laser light level over the scanned area of the object under inspection causes a consequential modulation of the acoustic image. This can be incorrectly interpreted as indicating variations in the acoustic properties of the object, whereas in fact there may be no such variations. There are a number of different possible causes for non-uniform scanning illumination. These include non-uniform deflection efficiency of the optical scanning system in scanner 20, misalignment of stage 21 relative to photodetector 37, non-uniformity of response over the active reception area of photodetector 37, and variations of reflectivity for different portions of the interface surface 29 of coverslip 28 or, in the instance of a polished surface test object, variations of reflectivity of the object surface.

Figure 5:
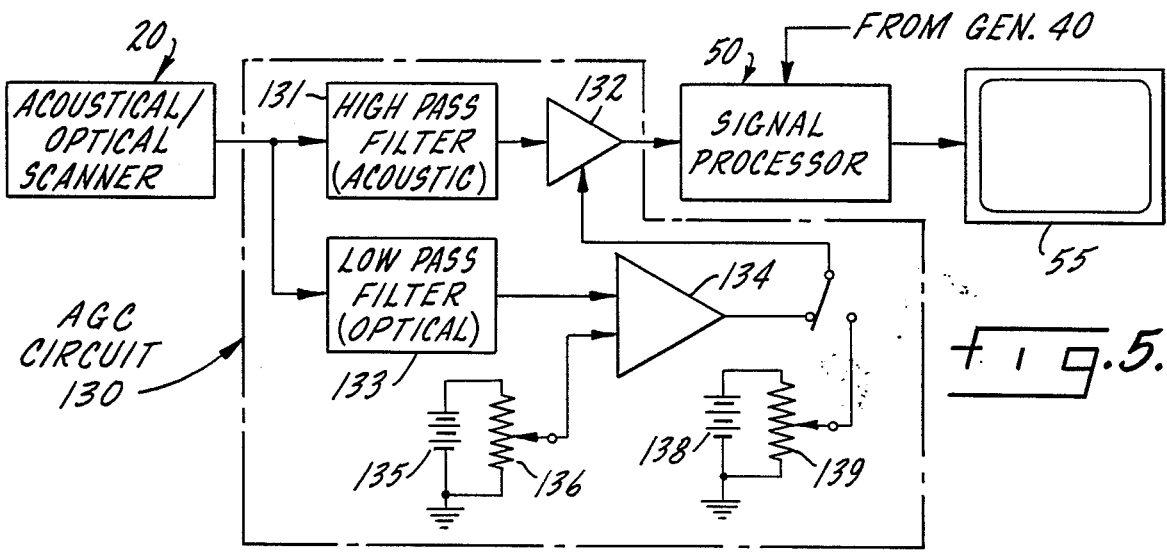
FIG. 5 illustrates a further modification of the acoustic imaging systems of FIGS. 1, 2 and 4, affording effective compensation for non-linearities in the optical scanners used in those systems.

FIG. 5 illustrates a system variation that may be utilized to compensate for non-uniformity of the laser scanning illumination level. The modification shown in FIG. 5 comprises an automatic gain control circuit 130 interposed between acoustic scanner 20 and signal processor 50. AGC circuit 130 includes a high pass filter 131 connected in series with an amplifier 132, the series combination of the circuits 131 and 132 being utilized to supply the high frequency components of the initial signal that is the output of scanner 20 to the input of signal processor 50. AGC circuit 130 further comprises a low pass filter 133 to which the initial signal from scanner 20 is supplied as an input; the output of filter 133 constitutes one input to a comparator amplifier 134. A second input to comparator 134 is a reference level signal derived from a variable DC source shown as a battery 135 and a potentiometer 136. The output of comparator 134 is connected through a selector switch 137 to a gain control input for amplifier 132. Selector switch 137 may also be utilized to connect the gain control input of amplifier 132 to a reference DC source shown as a battery 138 and a potentiomter 139.

The starting point for consideration of the operation of AGC circuit 130 is the fact that the acoustic information in the initial signal that is the output from scanner 20 is contained in the high frequency components of that signal. The low frequency components of the output signal from scanner 20 correspond to an optical image of the interface surface 29 (or the polished surface of a sample when that technique is used). Thus, the acoustical and optical information can be readily separated by means of filters 131 and 133.

In AGC circuit 130, the low frequency component of the output signal from acoustic scanner 20 is an optical content signal representing the effects of variations in performance of scanner 20, particularly deflector 32, coverslip 28 and interface surface 29, lenses 33 and 36, and photodetector 37 (FIG. 1). That optical content signal is supplied to comparator 134 for comparison with a reference signal level determined by reference source 135,136 (FIG. 5), so that comparator 134 develops a gain control signal. The gain control signal is utilized to increase the gain of amplifier 132 when the illumination level decreases and to decrease the gain when the illumination exceeds the reference level. The result is essentialy uniform sensitivity of system operation across the entire scanning field, effectively minimizing or eliminating non-uniformities of the optical scanning system as discussed above. Of course, the gain control arrangement of FIG. 5 can be applied to any of the quantitative measurement systems previously described; it can also be applied to a scanning laser acoustic microscope that affords only a qualitative output to improve performance by elimination of the effects of non-uniform optical scanning.

In the foregoing description, the light source used for optical scanning is described as a laser, and that is the preferred light source. However, any other high-intensity light source that can be focused to a small diameter scanning beam can be substituted. Further, although the imaging systems described above and shown in the drawings are "real time" systems, with a full image on display 55 being available to the system operator as soon as operation is commenced, the invention is also applicable to systems using slower scanners that require storage of image signal data before an image can be displayed.

We claim:

1. In an acoustic imaging system for generating a visual image representative of the acoustic properties of an object, of the kind including:
    insonification means for insonifying the object with acoustic waves having a frequency above ten megahertz to develop a pattern of perturbations on an at least partially light-reflective interface surface, coupled to the object, which pattern is representative of acoustic properties of the object;
    scanning means for scanning a high-energy small-diameter light beam across the interface surface;
    photodetection means for detecting a portion of the light beam reflected from the interface surface to develop an initial electrical signal;
    signal processor means, coupled to the photodetection means, for processing the initial electrical signal to develop an acoustic image signal;
    and display means, coupled to the signal processor means, for utilizing the image signal to develop a visual image representative of acoustic properties of the object;
    the improvement comprising:
    image signal level determination means, coupled to the signal processor means, for detecting the amplitude level of the image signal;
    and variable gain means, incorporated in the insonification means, for adjusting the intensity of the acoustic waves insonifying the object to afford an image signal level corresponding to a given reference level,
    the adjustment of the variable gain means affording a quantitative measure of variation of acoustic properties of the object, relative to the reference, that minimizes the effects of inadequate dynamic range and non-linearities in the imaging system.

2. An acoustic imaging system according to claim 1 in which the variable gain means comprises a signal-responsive variable gain circuit and indicator means for indicating the gain adjustment of the variable gain circuit.

3. An acoustic imaging system according to claim 2 in which the image signal level determination means is connected to the variable gain circuit to complete a closed loop for adjusting the variable gain circuit to maintain a substantially constant image signal level.

4. An acoustic imaging system according to claim 1, and further comprising: window gate means, interposed between the signal processor means and the image signal level determination means, for limiting the input to the level determination means to a predetermined portion of the image signal corresponding to a preselected limited portion of the scanned interface surface area so that the quantative measurement applies to a given limited portion of the object.

5. An acoustic imaging system according to claim 4, of the kind including a deflection signal generator means for generating horizontal and vertical deflection control signals H and V and supplying those signals to the scanning means and the display means to synchronize the scanning and display means, and further comprising:
    window logic means, coupled to the deflection signal generator means and to the window gate means and the display gate means, for generating window gate control signals H1 and V1 conjointly defining a predetermined portion of the image signal and supplying those gate control signals to the window gate means and the display gate means.

6. An acoustic imaging system according to claim 4, and further comprising:
   display gate means, coupled to the display means, for modifying the visual image to identify a predetermined limited portion of the visual image corresponding to the preselected portion of the scanned interface surface to which quantitative measurement is applicable.

7. An acoustic imaging system according to claim 6, and further comprising:
   second window gate means and second display gate means for adapting the imaging system to provide quantitative measurement of acoustic properties from a second limited portion of the scanned interface surface and identifying the corresponding portion of the visual image.

8. An acoustic imaging system according to claim 6, of the kind including a deflection signal generator means for generating horizontal and vertical deflection control signals H and V and supplying those signals to the scanning means and the display means to synchronize the scanning and display means, and further comprising:
   window logic means, coupled to the deflection signal generator means and to the window gate means and the display gate means, for generating window gate control signals H1 and V1 conjointly defining a predetermined portion of the image signal and supplying those gate control signals to the window gate means and the display gate means.

9. An acoustic imaging system according to claim 8, and further comprising:
   a source of a reference signal, connected to the display gate means; and
   adder means, in the image signal input to the display means, for adding the reference signal to the image signal to highlight a limited part of the visual image corresponding to the preselected portion of the scanned interface surface.

10. An acoustic imaging system according to claim 8, and further comprising:
    second window gate means and second display gate means and second window logic means, for adapting the imaging system to provide quantitative measurement of acoustic properties from a second limited portion of the scanned interface surface and identifying the corresponding portion of the visual image.

11. An acoustic imaging system according to claim 10, and further comprising:
    a source of a reference signal, connected to each of the display gate means; and
    adder means, in the image signal input to the display means, for adding the reference signal to the image signal to highlight limited parts of the visual image corresponding to the preselected portions of the scanned interface surface.

12. An acoustic imaging system according to claim 3, and further comprising: window gate means, interposed between the signal processor means and the image signal level determination means, for limiting the input to the level determination means to a predetermined portion of the image signal corresponding to a preselected limited portion of the scanned interface surface area so that the quantative measurement applies to a given limited portion of the object.

13. An acoustic imaging system according to claim 12, of the kind including a deflection signal generator means for generating horizontal and vertical deflection control signals H and V and supplying those signals to the scanning means and the display means to synchronize the scanning and display means, and further comprising:
    window logic means, coupled to the deflection signal generator means and to the window gate means and the display gate means, for generating window gate control signals H1 and V1 conjointly defining a predetermined portion of the image signal and supplying those gate control signals to the window gate means and the display gate means.

14. An acoustic imaging system according to claim 12, and further comprising:
    display gate means, coupled to the display means, for modifying the visual image to identify a predetermined limited portion of the visual image corresponding to the preselected portion of the scanned interface surface to which quantitative measurement is applicable.

15. An acoustic imaging system according to claim 14, and further comprising:
    second window gate means and second display gate means for adapting the imaging system to provide quantitative measurement of acoustic properties from a second limited portion of the scanned interface surface and identifying the corresponding portion of the visual image.

16. An acoustic imaging system according to claim 14, of the kind including a deflection signal generator means for generating horizontal and vertical deflection control signals H and V and supplying those signals to the scanning means and the display means to synchronize the scanning and display means, and further comprising:
    window logic means, coupled to the deflection signal generator means and to the window gate means and the display gate means, for generating window gate control signals H1 and V1 conjointly defining a predetermined portion of the image signal and supplying those gate control signals to the window gate means and the display gate means.

17. An acoustic imaging system according to claim 16, and further comprising:
    a source of a reference signal, connected to the display gate means; and
    adder means, in the image signal input to the display means, for adding the reference signal to the image signal to highlight a limited part of the visual image corresponding to the preselected portion of the scanned interface surface.

18. An acoustic imaging system according to claim 16, and further comprising:
    second window gate means and second display gate means, and second window logic means, for adapting the imaging system to provide quantitative measurement of acoustic properties from a second limited portion of the scanned interface surface and identifying the corresponding portion of the visual image.

19. An acoustic imaging system according to claim 17, and further comprising:
    a source of a reference signal, connected to each of the display gate means; and
    adder means, in the image signal input to the display means, for adding the reference signal to the image signal to highlight limited parts of the visual image corresponding to the preselected portions of the scanned interface surface.

20. An acoustic imaging system according to claim 1, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

21. An acoustic imaging system according to claim 20 in which a high pass filter is interposed between the photodetection means and the signal processor means, in series with the gain control means.

22. An acoustic imaging system according to claim 3, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

23. An acoustic imaging system according to claim 22 in which a high pass filter is interposed between the photodetection means and the signal processor means, in series with the gain control means.

24. An acoustic imaging system according to claim 6, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

25. An acoustic imaging system according to claim 24 in which a high pass filter is interposed between the photodetection means and the signal processor means, in series with the gain control means.

26. An acoustic imaging system according to claim 8, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

27. An acoustic imaging system according to claim 10, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

28. An acoustic imaging system according to claim 27 in which a high pass filter is interposed between the photodetection means and the signal processor means, in series with the gain control means.

29. An acoustic imaging system according to claim 16, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

30. An acoustic imaging system according to claim 29 in which a high pass filter is interposed between the photodetection means and the signal processor means, in series with the gain control means.

31. An acoustic imaging system according to claim 18, and further comprising an automatic gain control for optical effects, including:
   low pass filter means, coupled to the photodetection means, for developing an optical content signal from the initial electrical signal;
   comparator means for comparing the optical content signal with a given reference signal level to develop a gain control signal; and
   gain control means, interposed between the photodetection means and the signal processor means, responsive to the gain control signal, for varying the amplitude of the initial signal supplied to the signal processor means to minimize the effects of non-uniformity in operation of the scanning means and photodetection means.

32. An acoustic imaging system according to claim 31 in which a high pass filter is interposed between the photodetection means and the signal processor means, in series with the gain control means.

33. In an acoustic imaging system for generating a visual image representative of the acoustic properties of an object, of the kind including:
  insonification means for insonifying the object with acoustic waves having a frequency above ten megahertz to develop a pattern of perturbations on an at least partially light-reflective interface surface, coupled to the object, which pattern is representative of acoustic properties of the object;
  scanning means for scanning a high-energy small diameter light beam across the interface surface;
  photodetection means for detecting a portion of the light beam reflected from the interface surface to develop an initial electrical signal;
  signal processor means, coupled to the photodetection means, for processing the initial electrical signal to develop an acoustic image signal;
  and display means, coupled to the signal processor means, for utilizing the image signal to develop a visual image representative of acoustic properties of the object;
  the improvement comprising:
  low pass filter means, coupled to the photodetection means, for developing an optical content signal from the initial electrical signal;
  comparator means for comparing the optical content signal with a given reference signal level to develop a gain control signal; and
  gain control means, interposed between the photodetection means and the signal processor means, responsive to the gain control signal, for varying the amplitude of the initial signal supplied to the signal processor means to minimize the effects of non-uniformity in operation of the scanning means and photodetection means.

34. An acoustic imaging system according to claim 33, in which a high pass filter is interposed between the photodetection means and the signal processor means, in series with the gain control means.

35. In a method of acoustic imaging comprising the basic steps of:
  A. scanning a high-energy small-diameter light beam across an at least partially light-reflective interface surface coupled to an object to be examined;
  B. insonifying the object, concurrently with scanning step A with acoustic waves having a frequency above ten megahertz to develop a pattern of perturbations at the interface surface, which pattern is representative of acoustic properties of the object;
  C. detecting a portion of the light beam reflected from the interface surface to develop an initial electrical signal;
  D. processing the initial electrical signal to develop an acoustic image signal;
  E. and utilizing the image signal to develop a visual image representative of acoustic properties of the object;
  the improvement comprising:
  F. detecting the amplitude level of the image signal;
  G. adjusting the intensity of the acoustic waves insonifying the object to afford an image signal level corresponding to a given reference level; and
  H. recording the adjustment of acoustic wave intensity as a quantitative measure of variation of acoustic properties of the object, relative to the reference, that minimizes the effects of inadequate dynamic range and nonlinearities in the imaging system.

36. A method of acoustic imaging according to claim 35 in which:
  in step F the amplitude level of the detected image signal is integrated over a time interval no longer than the time required for a complete scan of the interface surface in step A and compared with a reference signal level to develop an acoustic gain control signal; and
  in step G the gain control signal is utilized to adjust the acoustic wave intensity.

37. A method of acoustic imaging according to claim 35 in which steps F, G and H are applied to a limited portion of the image signal corresponding to a predetermined limited part of the scanned interface surface.

38. A method of acoustic imaging according to claim 37 and further comprising:
  I. modifying the visual image, in step E, to afford visual identification of the limited part of the scanned interface surface to which steps F, G, and H are applied.

39. A method of acoustic imaging according to claim 35 in which steps F, G, and H are applied to two limited portions of the image signal corresponding to two predetermined limited parts of the scanned interface surface to permit quantitative comparison therebetween.

40. A method of acoustic imaging according to claim 39 and further comprising:
  I. modifying the visual image, in step E, to afford visual identification of the limited parts of the scanned interface to which steps F, G, and H are applied.

41. A method of acoustic imaging according to claim 36 in which steps F, G and H are applied to a limited portion of the image signal corresponding to a predetermined limited part of the scanned interface surface.

42. A method of acoustic imaging according to claim 41 and further comprising:
  I. modifying the visual image, in step E, to afford visual identification of the limited part of the scanned interface surface to which steps F, G, and H are applied.

43. A method of acoustic imaging according to claim 36 in which steps F, G, and H are applied to two limited portions of the image signal corresponding to two predetermined limited parts of the scanned interface surface to permit quantitative comparison therebetween.

44. A method of acoustic imaging according to claim 43 and further comprising:
  I. modifying the visual image, in step E, to afford visual identification of the limited parts of the scanned interface to which steps F, G, and H are applied.

45. A method of acoustic imaging according to claim 35, and further comprising:
  J. developing an optical content signal from the initial electrical signal of step C, using low pass filter means; and
  K. using the optical content signal to control the amplitude of the acoustic image signal to compensate for non-uniformities occurring in the scanning and detecting operations of steps A and C.

46. A method of acoustic imaging according to claim 36, and further comprising:
  J. developing an optical content signal from the initial electrical signal of step C, using low pass filter means; and K. using the optical content signal to control the amplitude of the acoustic image signal to compensate for non-uniformities occurring in the scanning and detecting operations of steps A and C.

47. A method of acoustic imaging according to claim 37, and further comprising:
J. developing an optical content signal from the initial electrical signal of step C, using low pass filter means; and
K. using the optical content signal to control the amplitude of the acoustic image signal to compensate for non-uniformities occurring in the scanning and detecting operations of steps A and C.

48. A method of acoustic imaging according to claim 38, and further comprising:
J. developing an optical content signal from the initial electrical signal of step C, using low pass filter means; and
K. using the optical content signal to control the amplitude of the acoustic image signal to compensate for non-uniformities occurring in the scanning and detecting operations of steps A and C.

49. A method of acoustic imaging according to claim 39, and further comprising:
J. developing an optical content signal from the initial electrical signal of step C, using low pass filter means; and
K. using the optical content signal to control the amplitude of the acoustic image signal to compensate for non-uniformities occurring in the scanning and detecting operations of steps A and C.

50. In a method of acoustic imaging comprising the basic steps of:
A. scanning a high-energy small-diameter light beam across and at least partially light-reflective interface surface coupled to an object to be examined;
B. insonifying the object, concurrently with scanning step A with acoustic waves having a frequency above ten megahertz to develop a pattern of perturbations at the interface surface, which pattern is representative of acoustic properties of the object;
C. detecting a portion of the light beam reflected from the interface surface to develop an initial electrical signal;
D. processing the initial electrical signal to develop an acoustic image signal;
E. and utilizing the image signal to develop a visual image representative of the acoustic properties of the object;
the improvement comprising:
J. developing an optical content signal from the initial electrical signal of step C, using low pass filter means; and
K. using the optical content signal to control the amplitude of the acoustic image signal to compensate for non-uniformities occurring in the scanning and detecting operations of steps A and C.

51. A method of acoustic imaging according to claim 50 in which step D is limited, by high pass filter means, to the higher frequency components of the initial electrical signal.

* * * * *